United States Patent [19]

McArdle et al.

[11] Patent Number: 5,138,644
[45] Date of Patent: Aug. 11, 1992

[54] METHOD AND APPARATUS FOR MEASURING THE WALL THICKNESS OF INSULATED PIPE

[75] Inventors: Joseph G. McArdle, N. Canton; Alan C. Magno, Barberton; Richard L. Krieger, Kent, all of Ohio

[73] Assignee: Glitsch Field Services/NDE, Inc., North Canton, Ohio

[21] Appl. No.: 237,295

[22] Filed: Aug. 26, 1988

[51] Int. Cl.$^5$ .............................................. G01B 15/02
[52] U.S. Cl. ........................................ 378/55; 378/54; 378/59
[58] Field of Search .................. 378/59, 60, 58, 57, 378/54, 55

[56] References Cited

U.S. PATENT DOCUMENTS

| | | | |
|---|---|---|---|
| 2,859,349 | 11/1958 | Bradley et al. | 250/53 |
| 3,080,479 | 3/1963 | Berg et al. | 378/59 |
| 3,278,747 | 10/1966 | Ohmart | 250/83.3 |
| 3,474,160 | 10/1969 | Doering | 264/40 |
| 3,489,901 | 1/1970 | Brown | 250/83.3 |
| 3,808,437 | 4/1974 | Miyagawa et al. | 250/359 |
| 4,088,886 | 5/1978 | Moulton | 250/277 R |
| 4,182,954 | 1/1980 | Giles | 250/308 |
| 4,542,297 | 9/1985 | Hold | 250/360.1 |
| 4,695,729 | 9/1987 | Monno et al. | 250/358.1 |

FOREIGN PATENT DOCUMENTS

2440274 12/1977 Fed. Rep. of Germany.
0008403 1/1982 Japan ................................. 378/59

Primary Examiner—David P. Porta
Attorney, Agent, or Firm—Michael Sand Co.

[57] ABSTRACT

A method and apparatus for measuring the wall thickness of insulated pipe of various sizes, shapes and locations without requiring removal of the insulation. The apparatus includes a source which emits a collimated beam of low-level radiation and a detector adapted to detect the beam. The source and detector are pivotally mounted on trucks which in turn are movably mounted on frame assemblies which include rotatable shafts. Stepping motors are mounted on the frame assemblies and are drivingly connected to the shafts for rotating the shafts. Indexer devices are connected to a computer and to the motors for controlling the rotation of the shafts. Motion translators are mounted on the trucks and are operatively connected to the shafts for translating the rotational motion of the shafts into linear motion. The source and detector are located in aligned, opposed spaced relationship adjacent to the pipe. The stepping motors simultaneously linearly move the trucks, and the source and detector mounted thereon, in discrete linear steps along the shafts for scanning the pipe to take discrete measurements of the pipe wall thickness. The radiation beam emitted by the source passes through the insulated pipe and is detected by the aligned detector at each discrete step. A single channel analyzer device connected to the detector measures counts of unattenuated radiation beams detected by the detector. A computer is connected to the single channel analyzer through an interface and generates computer profiles of the pipe wall thickness.

11 Claims, 6 Drawing Sheets

RADIAL DISTANCE

Fig. 10

METHOD AND APPARATUS FOR MEASURING THE WALL THICKNESS OF INSULATED PIPE

TECHNICAL FIELD

The invention relates to measuring devices and in particular to a method and apparatus for measuring the wall thickness of insulated pipe. More particularly, the invention relates to such a method and apparatus in which the wall thickness of insulated pipe of various sizes, shapes and locations can be measured without removing the insulation therefrom.

BACKGROUND ART

The thinning of pipe walls in nuclear power plants recently has been recognized as a serious industrywide problem. More specifically, it has been discovered that carbon steel pipe, which carries wet steam in nuclear power plants, is especially susceptible to erosion and corrosion. In some instances, pipe wall thicknesses have been reduced at a rate of 1.0 to 1.5 millimeters per year, yet many plants do not have in place an inspection program for examining the thickness of the pipe walls. Such pipe wall degradation rates, at best, are severe enough to cause pipe failures resulting in costly repairs and plant downtime. At worst, plant workers could be injured or killed. Thus, it can be seen that pipe wall thickness inspections are necessary to detect and periodically monitor the severity of such degradation, and in fact now are required of all nuclear power plant licensees by the United States Nuclear Regulatory Commission.

However, virtually all carbon steel piping carrying wet steam in nuclear power plants is insulated to minimize heat loss. Thus, all known current inspection techniques, such as the ultrasonic method, require costly insulation removal and site preparation in order to measure the pipe wall degradation. If the insulation is asbestos, as is the case in many plants, inspection can be further complicated due to the health hazards associated therewith.

The known prior art includes various methods and apparatus which utilize radiation for measuring the wall thickness of a pipe or the thickness of other objects such as a sheet or strip of material,etc. Such known prior art is disclosed in U.S. Pat. Nos. 2,859,349; 3,808,437; 4,088,886; 4,182,954; 4,542,297; and 4,695,729. However, the apparatus, methods and results obtained by the inventions shown therein are completely different than the apparatus, method and objectives achieved by our invention. More specifically, the disclosure of these patents includes a plurality of radiation sources and/or detectors, the necessity of moving the object being measured, elongated sources and/or detectors, obtaining measurements of average thickness, use of a relatively high-level radiation source, etc.

The known prior art also shows methods and apparatus for weighing material using radiation. Such known methods and apparatus are disclosed in U.S. Pat. Nos. 3,278,747 and 3,489,901. Again, however, such methods and apparatus require movement of the material being measured and utilize multiple and elongated sources and detectors.

The closest known prior art to our present invention is shown in U.S. Pat. No. 3,474,160. However, the method and apparatus shown and described in this patent is considerably different than our invention. First, the source and detector of the apparatus disclosed in this '160 patent continuously move back and forth across the sheet being measured to take continuous measurements of the sheet thickness. In contrast, the source and detector of the present invention move in discrete linear steps for scanning a pipe to take discrete measurements of the pipe wall thickness. In addition, the source and detector shown in the '160 patent are mounted on traversing rods which extend between mounting brackets, with the source and detector being directly driven by a traversing motor. In comparison, the source and detector of the present invention each is mounted on its own frame assembly. Elongated rotatable shafts of the frame assemblies are operatively connected to the source and detector. A motor rotates the shafts and means are utilized for translating the rotational motion of the shafts into the linear motion of the source and detector.

Therefore, the need exists for a method and apparatus for measuring the wall thickness of insulated pipe of various shapes, sizes and locations, without requiring costly insulation removal and site preparation.

DISCLOSURE OF THE INVENTION

Objectives of the invention include providing a method and apparatus for measuring the wall thickness of insulated pipe.

Objectives of the invention further include providing such a method and apparatus which can be used to successfully, periodically monitor pipe systems, in industries which employ susceptible pipe systems, for erosion/corrosion without requiring inordinate set up costs including insulation removal and site preparation.

Another objective of the invention is to provide such a method and apparatus which is adapted to measure the wall thickness of pipes of varying sizes, shapes and locations, while substantially reducing the possibility of human error entering into such measurements.

Still another objective of the invention is to provide such a method and apparatus capable of measuring the wall thickness of a pipe whether the pipe is full or empty; and in which a further objective of the invention is to provide such a method and apparatus which can detect obstructions in a pipe, and which can differentiate between heterogeneous objects and substances.

A further objective of the invention is to provide such a method and apparatus which can successfully monitor plant pipe systems to substantially reduce or eliminate pipe failures resulting in costly repairs, plant downtime and personal injuries and fatalities.

A still further objective of the invention is to provide such a method and apparatus which utilizes relatively low curie levels of radiation and which substantially reduces or eliminates "scatter" radiation while the apparatus is in use for safety purposes.

Another objective of the invention is to provide such a method and apparatus adapted to measure pipes having a diameter or width of approximately six inches to forty-two inches.

Still another objective of the invention is to provide such a method and apparatus which is economical to manufacture, portable, easy to set up and operate, durable in use, and accurate.

These objectives and advantages are obtained by the method of the invention, the general nature of which may be stated as including a method of measuring the wall thickness of a pipe surrounded by insulation without removing the insulation therefrom, the method including the steps of, locating a radiation source and a radiation detector in aligned, opposed spaced relationship, so that a collimated beam of radiation emitted by the source passes through the insulation and pipe and is detected by the detector, and simultaneously moving the source and the detector in discrete linear steps for scanning the pipe to take discrete measurements of the pipe wall thickness, the detector providing data for profiles of the pipe wall thickness.

The objectives and advantages are further obtained by the apparatus of the invention, the general nature of which may be stated as including an apparatus for measuring the wall thickness of an insulated pipe without removing the insulation therefrom, the apparatus including a source for emitting a collimated beam of radiation, a detector for detecting the radiation beam, a pair of frame assemblies, the assemblies each adapted for movably mounting a respective one of the source and detector, the assemblies each including an elongated rotatable shaft operatively connected to the respective one of the source and detector, means for rotating the shafts, and means for translating the rotational motion of the shafts into linear motion to simultaneously linearly move the source and detector in discrete steps for scanning the pipe to take measurements of the pipe wall thickness.

BRIEF DESCRIPTION OF THE DRAWINGS

A preferred embodiment of the invention, illustrative of the best mode in which applicants have contemplated applying the principles, is set forth in the following description and is shown in the drawings and is particularly and distinctly pointed out and set forth in the appended claims.

Similar numerals refer to similar parts throughout the drawings.

BEST MODE FOR CARRYING OUT THE INVENTION

Figure 1:
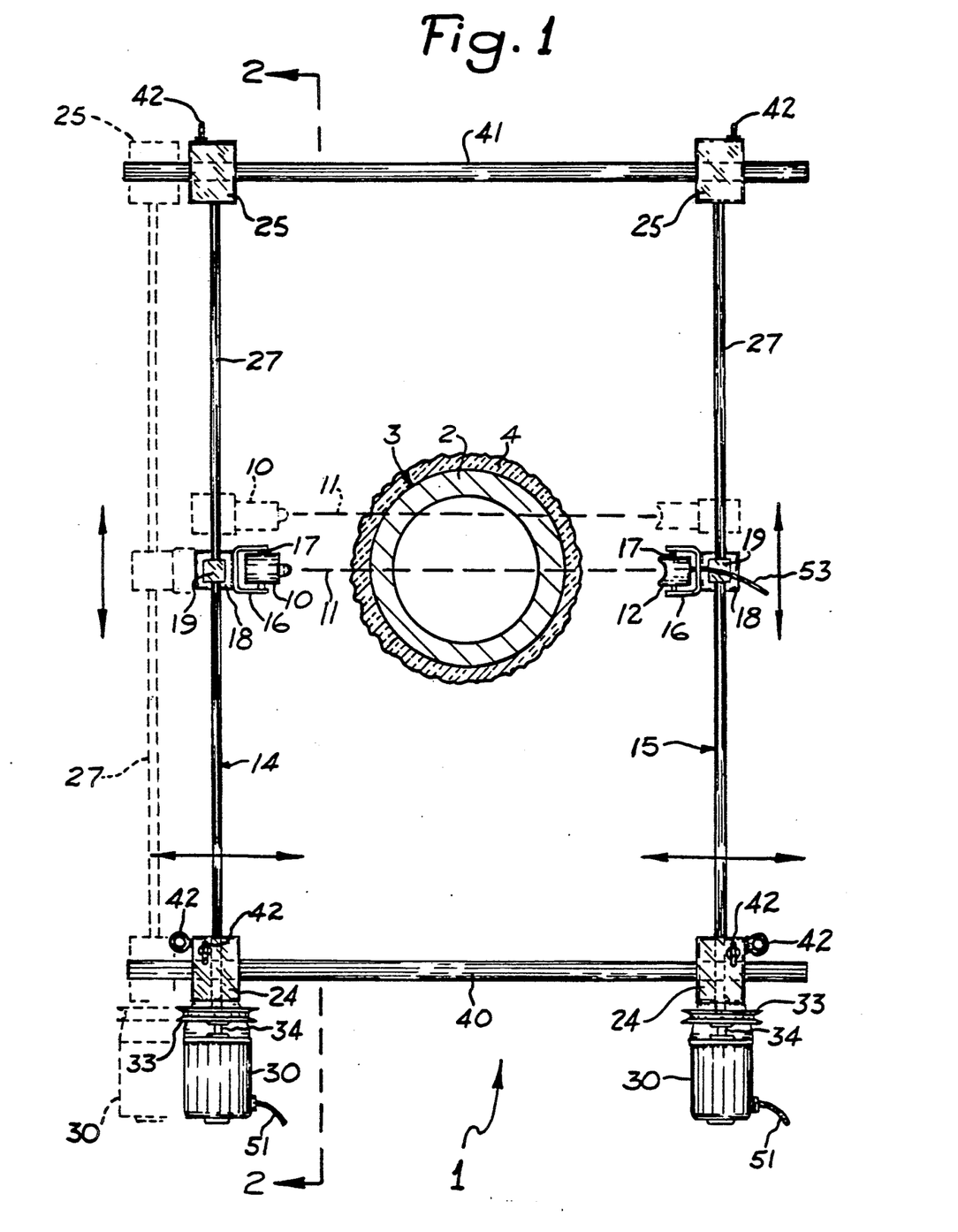
FIG. 1 is a fragmentary top plan view of the apparatus of the present invention, shown measuring the wall thickness of a section of insulated pipe.

The apparatus of the present invention is indicated generally at 1, and is shown in FIG. 1 measuring the thickness of a wall 2 of a pipe 3 surrounded by insulation 4. Apparatus 1 is intended primarily for use in detecting and periodically monitoring the severity of pipe wall thinning in areas of two phase flow of water and steam in pipe used in nuclear power plants, and more specifically in "hot crossover piping" where turbulent flow occurs. However, apparatus 1 also may be used for inspecting pipe systems in fossil fuel and chemical/petro-chemical plants, as well as other applications. Apparatus 1 includes a source 10 for emitting a collimated beam of radiation 11. The radiation source preferably is cesium having a curie value or energy level of less than 200 millicuries for safety purposes. A source meeting these specifications is the "Master Minder" source manufactured by Gamma Industries, a division of Nuclear Systems, Inc. A detector 12 for detecting or receiving radiation beam 11 also is included in apparatus 1, and preferably is the model 44-2 gamma scintillator manufactured by Ludlum Measurements, Inc. of Sweetwater, Tex.

Figure 2:
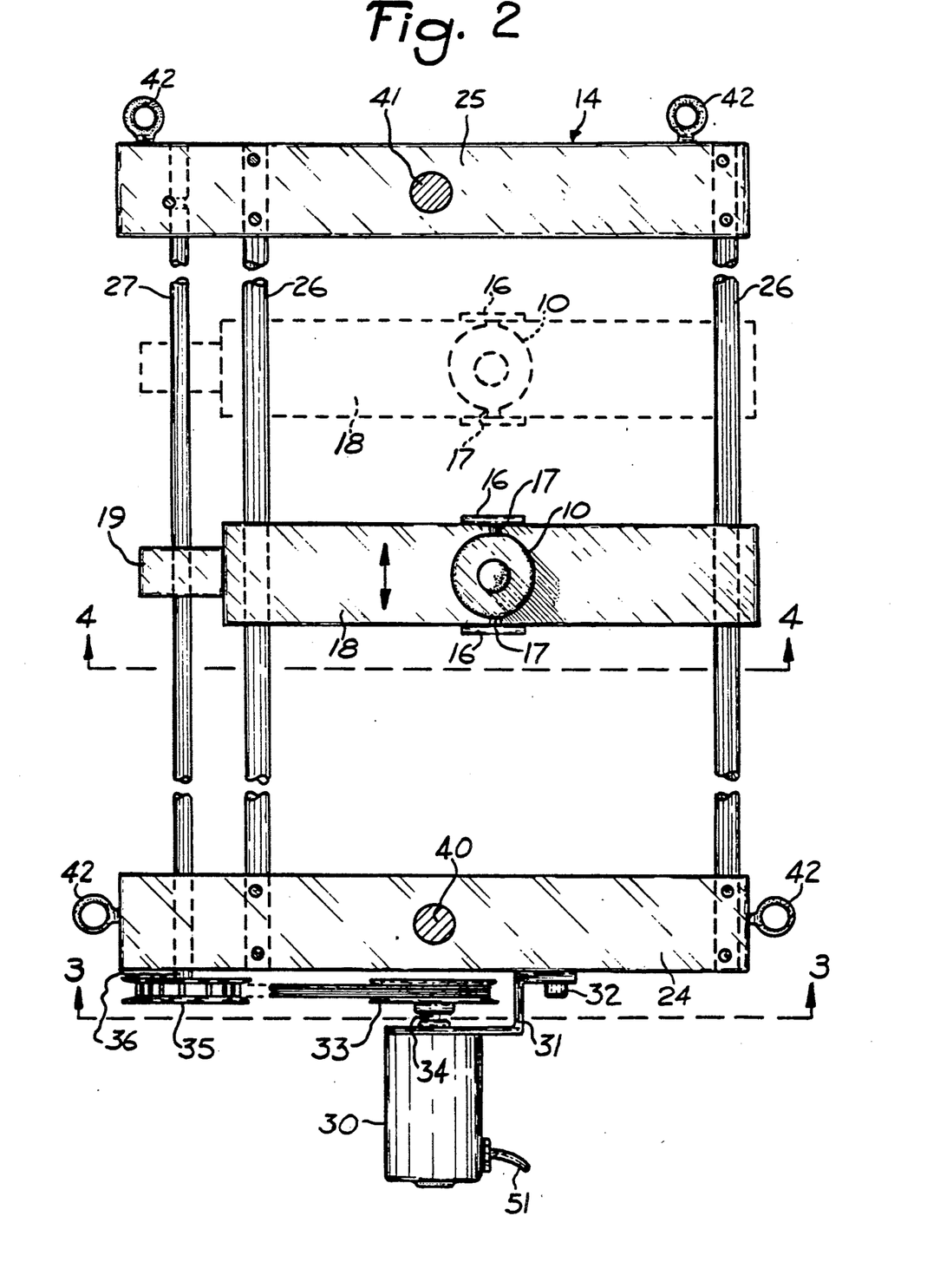
FIG. 2 is an enlarged, fragmentary sectional view, with portions broken away, of the source frame assembly, taken on line 2—2, FIG. 1.
Figure 4:
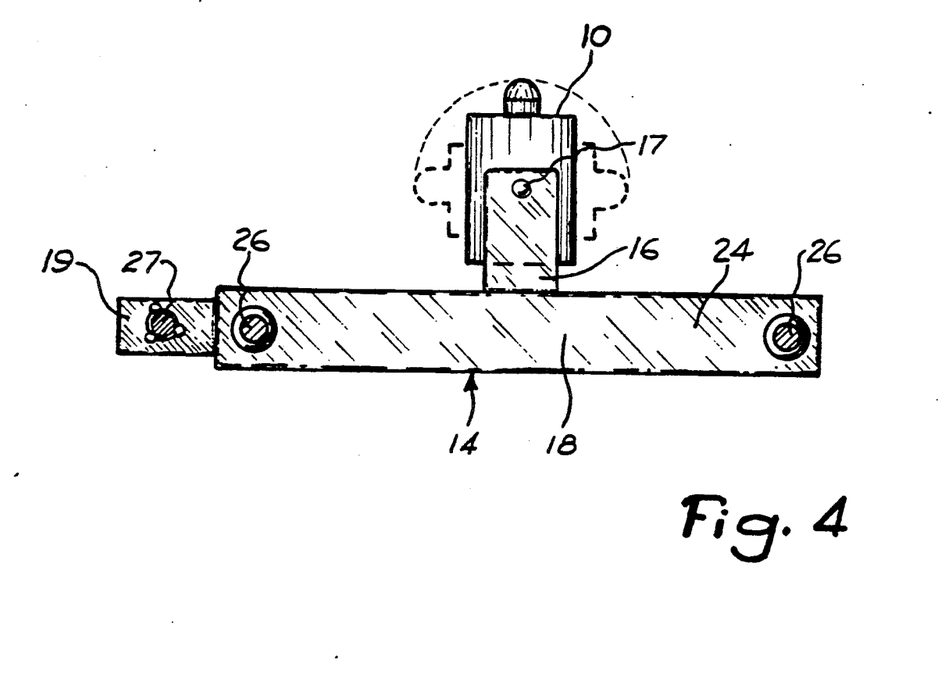
FIG. 4 is a sectional view taken on line 4—4, FIG. 2, particularly showing the range of pivotal movement of the source on the truck.

Source 10 and detector 12 are mounted on similar frame assemblies 14 and 15 (FIG. 1), respectively, so that only the mounting of source 10 on frame assembly 14 will be described in detail herein. Source 10 is pivotally mounted on a pivot stand 16 by a pair of pivot pins 17 (FIG. 2). Pivot stand 16 in turn is mounted on a truck 18 by any suitable means. Thus, source 10 can be pivoted through 180 degrees, as shown in FIG. 4 in phantom lines, providing greater flexibility of use to apparatus 1 for taking measurements. A motion translator 19 of a type well-known in the art is attached to truck 18.

In accordance with one of the main features of the invention, frame assembly 14 comprises a drive block 24, a bearing block 25, a pair of spaced, parallel elongated rails 26, and an elongated rotatable shaft 27 which is spaced from and parallel to rails 26 (FIG. 2). Drive block 24 is spaced from and parallel to bearing block 25, and both of the blocks are transverse to the longitudinally extending rails 26 and shaft 27. Rails 26 extend between and are mounted on drive and bearing blocks 24 and 25, and shaft 27 extends between and is rotatably mounted on the blocks. Truck 18 is movably mounted on rails 26. Motion translator 19, the purpose of which will be described in greater detail below, is operatively connected to shaft 27.

Figure 3:
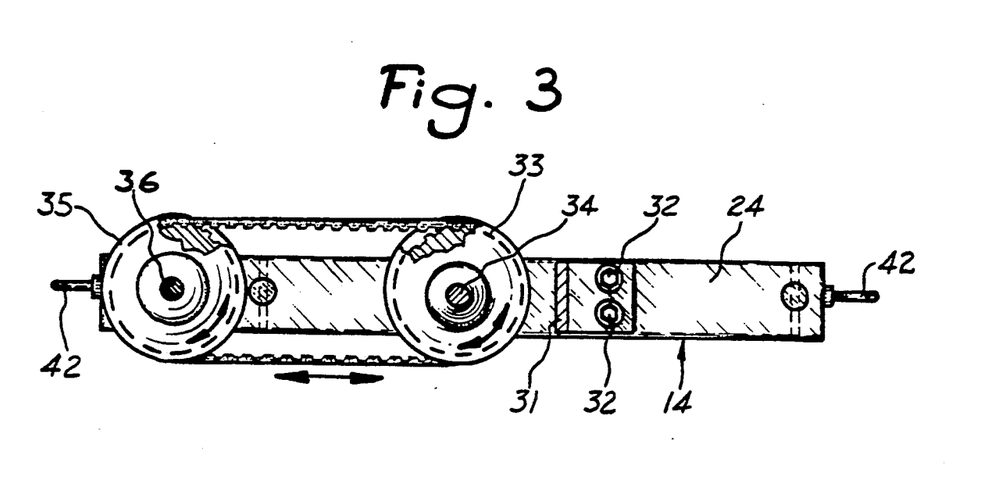
FIG. 3 is a sectional view, with portions broken away, taken on line 3—3, FIG. 2, particularly showing the pulleys and timing belt assembly.

A stepping motor 30 is mounted on a motor bracket 31 which in turn is mounted on drive block 24 of frame assembly 14 by a pair of bolts 32 (FIGS. 2 and 3). A first timing belt pulley 33 is attached to an output shaft 34 of motor 30, and a second timing belt pulley 35 is attached to an end 36 of shaft 27 which extends through drive block 24. A timing belt 37 extends between pulleys 33 and 35 to drivingly connect motor 30 to shaft 27 for rotating the shaft.

Figure 5:
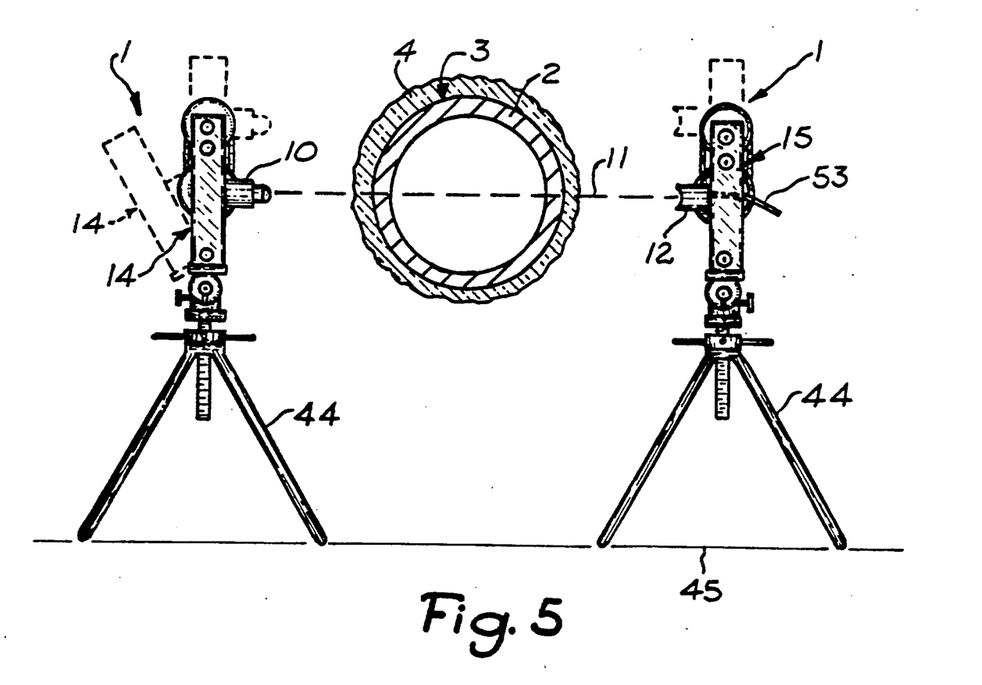
FIG. 5 is an end view of the apparatus of the invention, showing the source and detector frame assemblies pivotally mounted on and elevated by support stands for taking a measurement of an insulated section of pipe.
Figure 6:
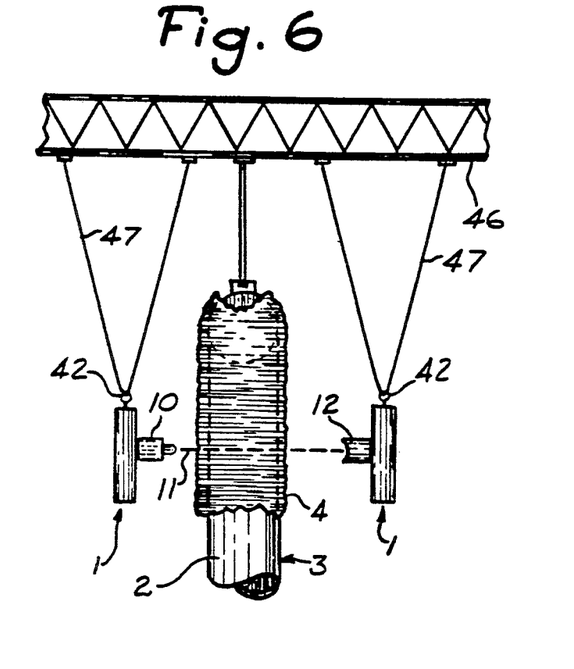
FIG. 6 is a diagrammatic view showing the detector and source frame assemblies suspended from a ceiling for taking a measurement.

Drive blocks 24 of frame assemblies 14 and 15 can be slideably adjustably mounted on a first tie rod 40 and bearing blocks 25 of the frame assemblies can be similarly slideably adjustably mounted on a second tie rod 41, if it is desired to securely interconnect frame assemblies 14 and 15 in a spaced relationship (FIG. 1). The slideable mounting of drive and bearing blocks 24 and 25 on tie rods 40 and 41, respectively, also provides for adjustment of the spacing between source 10 and detector 12, as shown in dot-dash lines in FIG. 1. The direction of adjustment of frame assemblies 14 and 15 is indicated by the horizontal arrows of FIG. 1. However, it may be desired to locate frame assemblies 14 and 15 independent of one another for taking a measurement, as shown in FIGS. 5 and 6. The location of the pipe to be measured, as well as other factors, will determine whether tie rods 40 and 41 should be utilized.

A plurality of eye bolts 42 (FIGS. 1-3) are mounted on drive blocks 24 and bearing blocks 25 of frame assemblies 14 and 15 for locating source 10 and detector 12 adjacent to a pipe for taking a measurement, as explained below in the description of the operation of apparatus 1.

The method for measuring the wall thickness of a pipe surrounded by insulation using apparatus 1 is set forth below. Frame assemblies 14 and 15 are located adjacent to the pipe to be measured. Source 10 and detector 12 are aligned in opposed spaced relationship so that collimated radiation beam 11 emitted by source 10 passes through insulation 4 and pipe 3 and is detected by the detector, as best shown in FIG. 1. Pipe 3 preferably is empty during this operation, but can be full of wet steam or another substance without affecting the measuring capabilities of the apparatus. Locating the frame assemblies adjacent to the pipe to be measured and aligning the source and detector can be achieved in a variety of ways, but the manner chosen depends on the particular location of the pipe. Two ways of achieving such proper location and alignment are shown in FIGS. 5 and 6. In FIG. 5, the bearing blocks and drive blocks of the frame assemblies are pivotally mounted on support stands 44. It can be seen that support stands 44, which have adjustable elevations, can be used to elevate the source and detector off of ground 45 or other support surface when the inspected pipe is adjacent to the ground or other surface.

When the monitored pipe is at a location which cannot be reached by elevating the source and detector, such as when the pipe is suspended from a ceiling 46 as illustrated in FIG. 6, the source and detector can be positioned adjacent to the pipe and aligned by independently suspending the frame assemblies by cables 47 which are attached to certain ones of eye bolts 42 and the ceiling.

Figure 10:
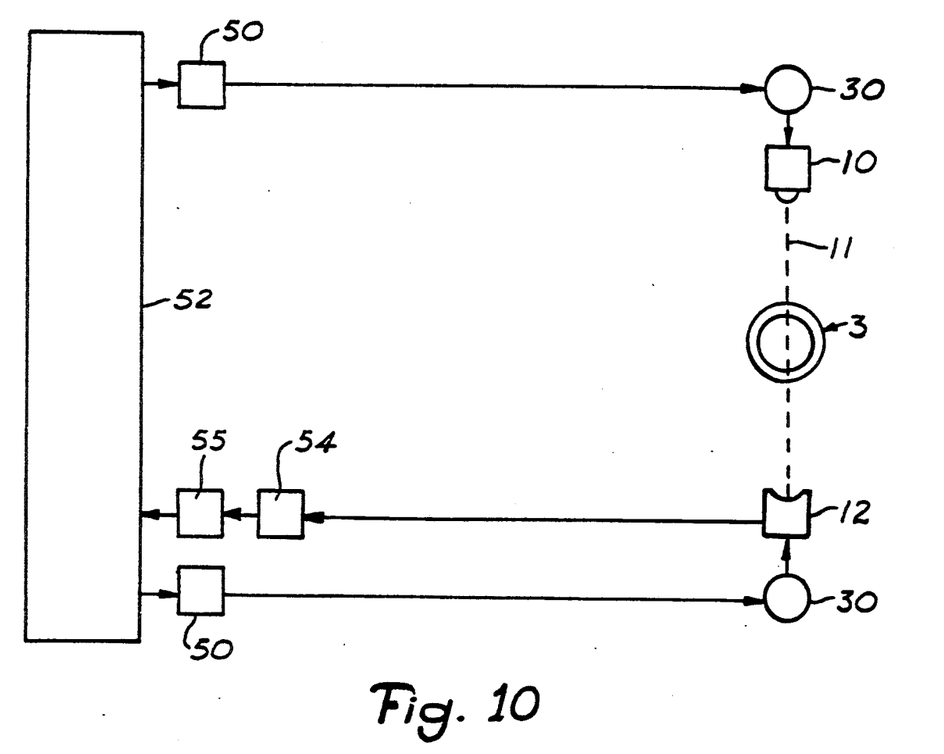
FIG. 10 is a block diagram of the apparatus of the invention.

In accordance with another principal feature of the invention, after proper positioning of the frame assemblies and alignment of the source and detector, motors 30 are actuated to rotate shafts 27 of the frame assemblies. Referring now to FIG. 10, motors 30 are connected to indexer devices 50 by electrical cables 51 (FIG. 1). Indexers 50 in turn are electrically connected to a computer 52. Computer 52 and indexers 50 cooperate to pulse predetermined amounts of electrical current to motors 30 for rotating shafts 27. The rotational motion of shafts 27 is translated into linear motion by motion translators 19 for simultaneously linearly moving trucks 18, and the source and detector mounted thereon, along rails 26 of the frame assemblies to take discrete measurements of the pipe wall thickness. The source and detector preferably move in one-eighth inch increments or steps. Thus, the source and detector simultaneously linearly move in the same direction and remain in alignment for each discrete measurement.

The detector then provides data, based on the level of radiation emitted by the source which passes through the pipe and insulation and reaches the detector, for profiles of the pipe wall thickness. More particularly, and again referring to FIG. 10, the detector is connected by an electrical cable 53 (FIG. 1) to a single channel analyzer device 54 which in turn is connected to computer 52 through an interface device 55 of a type well-known in the art. Device 54 preferably is the model 2200 single channel analyzer manufactured by Ludlum Measurements Inc. of Sweetwater, Tex.

When the detector is scintillated by radiation from the source, single channel analyzer 54 translates such scintillations into counts. The single channel analyzer measures only unattenuated radiation beams from the source, that is, beams having an energy level which falls between two discrete, relatively low energy levels. This enables a source having radiation levels of less than 200 millicuries to be used. Many prior art radiation measuring devices, on the other hand, utilize ratemeters which measure counts per minute and require sources having high radiation levels. Moreover, detecting only unattenuated or "unscathed" radiation beams increases the measuring sensitivity of apparatus 1, since "background noise" or attenuated radiation beams received by the detector are virtually eliminated from the counts produced by the single channel analyzer.

The counts from the single channel analyzer are relayed to computer 52 through interface 55 for generating position-count profiles of the pipe wall thickness. It is understood that such profiles can be achieved by a technician recording the count readings from the digital readout of the single channel analyzer. However, the former computer method is preferred to substantially eliminate human error which could occur in connection with recording and plotting the count readings from the single channel analyzer. Moreover, each discrete measurement is taken quickly, preferably in approximately eleven seconds, with the detector detecting radiation for six seconds, and the single channel analyzer and computer processing the data for five seconds while the source and detector move to the next measurement step.

Figure 8:
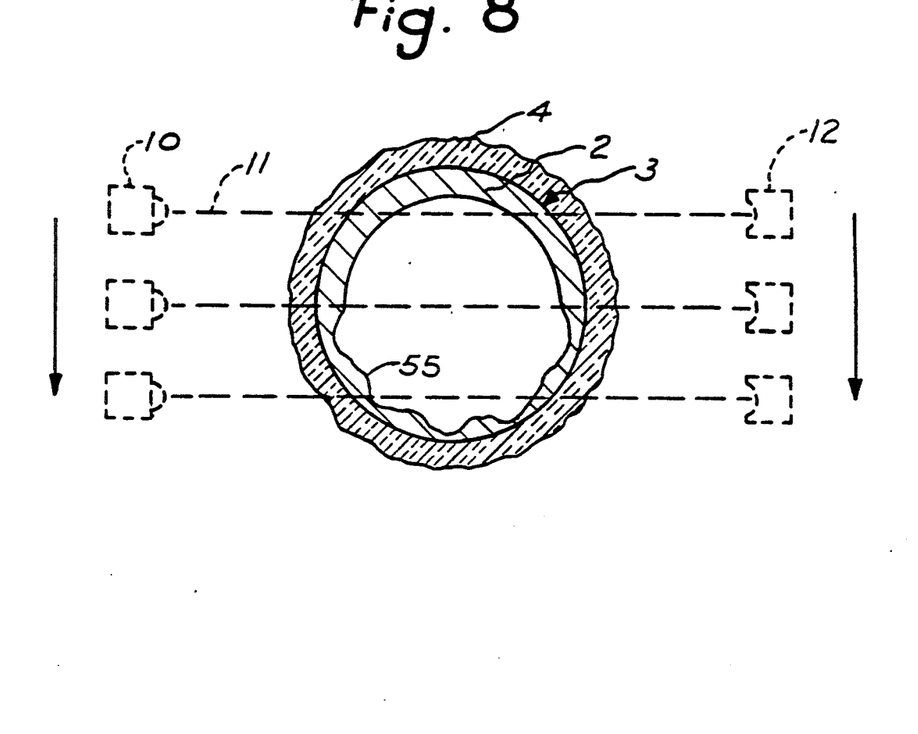
FIG. 8 is an enlarged diagrammatic view of the source and detector taking discrete measurements of a corroded pipe.
Figure 9:
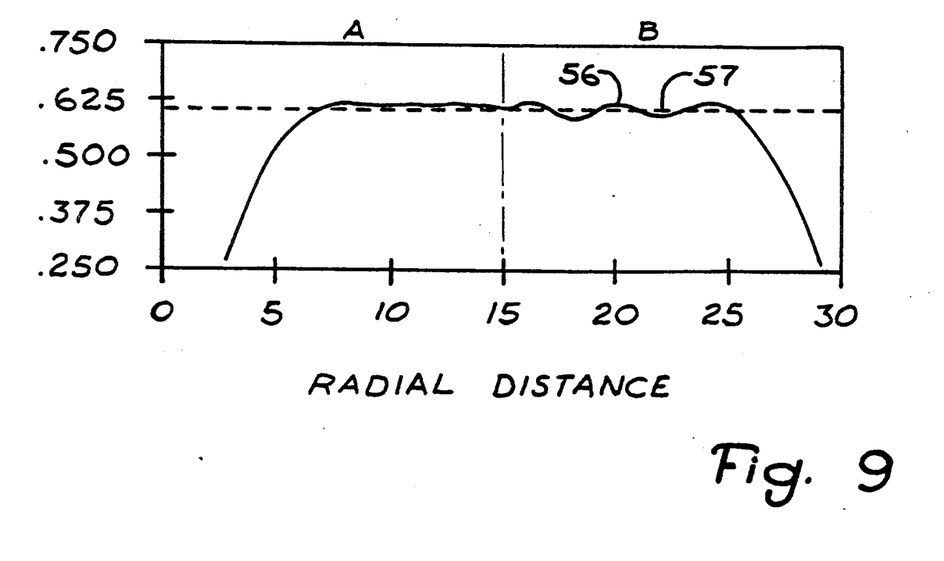
FIG. 9 is a computer-generated profile of the pipe wall thickness of the corroded pipe of FIG. 8.

The measurement of a hypothetical insulated pipe by apparatus 1 is shown schematically in FIG. 8, with the pipe wall thickness profiles generated therefrom being shown in FIG. 9. As the source and detector simultaneously scan the insulated pipe in discrete linear steps in the direction of the vertical arrows of FIG. 8, an eroded or corroded wall 55 is detected and represented, after computer manipulation of the data from the single channel analyzer including correction for differences in the material forming the insulation and pipe, as the oscillating solid line 56 about the horizontal dot-dash line 57 in the right-hand portion B of the graph of FIG. 9. In comparison, the uncorroded portion of the same pipe is represented in the left-hand portion A of the same graph.

Figure 7:
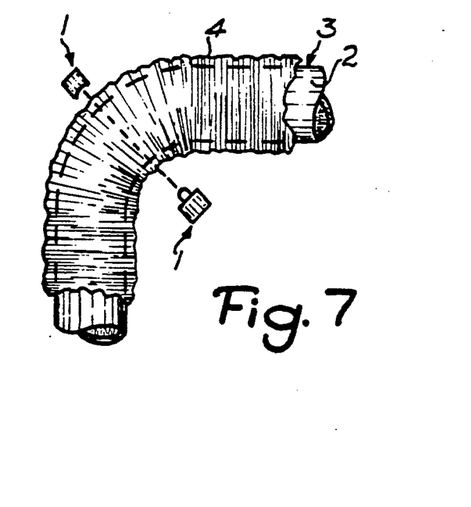
FIG. 7 is a diagrammatic view showing the source and detector taking a measurement at an elbow of an insulated pipe.

The above-described simultaneous linear movement of the source and detector is especially useful for taking measurements of a pipe having a bend therein as shown in FIG. 7. Furthermore, this method of linear scanning achieved by the apparatus of the invention can be used to scan pipes of varying sizes and shapes, a result not possible with many prior art scanning devices, and especially those of the circular scanning type. More particularly, a circular scanning approach would require a more elaborate scanning device than the present invention and/or many different sized apparatus.

It is understood that the apparatus and method of the present invention is not limited to measuring pipe wall thicknesses, but can also be used to detect obstructions in a pipe and differentiate between heterogeneous objects and substances.

Thus, it can be seen that the method and apparatus for measuring the wall thickness of insulated pipe can be used to successfully, periodically monitor pipe systems, and particularly pipe systems which are susceptible to erosion and corrosion, without requiring inordinate set up costs including insulation removal and site preparation. In addition, the linear scanning method and apparatus is adapted to measure the wall thickness of pipes of varying sizes and shapes, and of pipes located in hard-to-reach locations. The method and apparatus also can measure the wall thickness of a pipe whether the pipe is full or empty, and can detect obstructions in a pipe and differentiate between heterogeneous objects and substances. The invention described herein can successfully monitor plant pipe systems to substantially reduce or eliminate pipe failures which could result in costly repairs, plant downtime and personal injuries and/or fatalities. Moreover, the present invention utilizes low curie levels of radiation and substantially reduces or eliminates "scatter" radiation which makes the apparatus inherently safe to use. Finally, the invention is economical to manufacture, portable, easy to set up and operate, durable in use, and accurate.

Accordingly, the method and apparatus for measuring the wall thickness of insulated pipe is simplified, provides an effective, safe, inexpensive, and efficient method and apparatus which achieves all the enumerated objectives, provides for eliminating difficulties encountered with prior methods and apparatus, and solves problems and obtains new results in the art.

In the foregoing description, certain terms have been used for brevity, clearness and understanding; but no unnecessary limitations are to be implied therefrom beyond the requirements of the prior art, because such terms are used for descriptive purposes and are intended to be broadly construed.

Moreover, the description and illustration of the invention is by way of example, and the scope of the invention is not limited to the exact details shown or described.

Having now described the features, discoveries and principles of the invention, the manner in which the apparatus and method is constructed and carried out, the characteristics of the apparatus and method, and the advantageous, new and useful results obtained; the new and useful structures, devices, elements, arrangements, parts, methods, and combinations, are set forth in the appended claims.

What is claimed is:

1. A method of measuring the wall thickness of an insulated pipe without removing the insulation therefrom, said method including the steps of:
    a) locating a generally low-level radiation source and a radiation detector in aligned, opposed spaced relationship, so that a collimated beam of radiation emitted by said source passes through the insulated pipe and is received in an unattenuated condition by said detector;
    b) simultaneously linearly moving the source and the detector in discrete linear steps for scanning the pipe to take discrete measurements of the pipe wall thickness;
    c) recording a radiation count at each of the discrete linear steps from a single channel analyzer device connected to the detector;
    d) interfacing the single channel analyzer with a computer to provide data to the computer; and
    e) generating a profile of the pipe wall thickness from the data provided to the computer.

2. An apparatus for measuring the wall thickness of an insulated pipe without removing the insulation therefrom, said apparatus including:
    a) a source for emitting a collimated beam of radiation;
    b) a detector for detecting said radiation beam;
    c) a pair of frame assemblies for movably mounting the source and detector, said assemblies each including an elongated rotatable shaft operatively connected to a respective one of the source and detector;
    d) means for rotating the shafts;
    e) means for translating the rotational motion of the shafts into linear motion to simultaneously linearly move the source and detector in discrete steps for scanning the pipe to take discrete measurements of the pipe wall thickness;
    f) a single channel analyzer device electrically connected to the detector for measuring counts of unattenuated radiation beams detected by said detector; and
    g) a computer electrically connected to the single channel analyzer, so that a computer profile of the pipe wall thickness is generated from the unattenuated radiation beam counts measured by the single channel analyzer.

3. The apparatus defined in claim 2 in which each of the pair of frame assemblies comprises a drive block, a bearing block, a pair of spaced, parallel elongated rails, and the elongated rotatable shaft; in which the elongated shaft is spaced from and parallel to the pair of rails; in which the drive block is spaced from and parallel to the bearing block and said drive and bearing blocks are transverse to the longitudinally extending rails and shaft; in which the pair of rails extend between and are mounted on the drive block and bearing block; and in which the elongated shaft extends between and is rotatably mounted on the drive and bearing blocks.

4. The apparatus defined in claim 3 in which the source and the detector each is pivotally mounted on a truck; and in which each of the trucks is movably mounted on the pair of rails of a respective one of the frame assemblies.

5. The apparatus defined in claim 4 in which the means for translating the rotational motion of the shafts into linear motion is a pair of motion translators; and in which each of said motion translators is mounted on a respective one of the trucks and is operatively connected to a respective one of the shafts.

6. The apparatus defined in claim 3 in which the means for rotating the shafts is a pair of stepping motors; in which each of the stepping motors is mounted on the drive block of a respective one of the frame assemblies and includes an output shaft and a first pulley attached to said output shaft; in which a second pulley is attached to an end of each of the elongated shafts which extends through the drive block of its respective frame assembly; and in which an endless timing belt extends between and drivingly connects each of the motors to a respective one of the elongated shafts.

7. The apparatus defined in claim 3 in which the drive blocks of the frame assemblies are slideably adjustably mounted on a first tie rod and the bearing blocks of said frame assemblies are slideably adjustably mounted on a second tie rod, for securely interconnecting said frame assemblies in a spaced relationship and for varying said spaced relationship to effect varying spacings between the source and detector.

8. The apparatus defined in claim 3 in which a plurality of eye bolts are mounted on the drive blocks and bearing blocks of the frame assemblies; and in which each of the frame assemblies is suspended from at least one cable attached to certain ones of the eye bolts and to another object for locating the source and detector adjacent to a pipe for taking a measurement.

9. The apparatus defined in claim 3 in which the bearing blocks and drive blocks of the frame assemblies each is pivotally mounted on a support stand for elevating said frame assemblies for locating the source and detector adjacent to a pipe for taking a measurement.

10. The apparatus defined in claim 2 in which the source generally has a radiation level of less than 200 millicuries.

11. The apparatus defined in claim 2 in which at least one indexer device is electrically connected to the computer and to the means for rotating the frame assembly shafts for controlling the linear movement of the source and detector.

* * * * *